United States Patent [19]

Fountain

[11] Patent Number: 5,286,964

[45] Date of Patent: * Feb. 15, 1994

[54] SYSTEM FOR DETECTING, CORRECTING AND MEASURING DEPTH MOVEMENT OF A TARGET

[75] Inventor: William D. Fountain, Fremont, Calif.

[73] Assignee: Phoenix Laser Systems, Inc., Fremont, Calif.

[*] Notice: The portion of the term of this patent subsequent to Nov. 10, 2009 has been disclaimed.

[21] Appl. No.: 945,207

[22] Filed: Sep. 15, 1992

Related U.S. Application Data

[63] Continuation-in-part of Ser. No. 655,919, Feb. 19, 1991, Pat. No. 5,162,641.

[51] Int. Cl.$^5$ .............................................. G01S 17/08
[52] U.S. Cl. ................................. 250/201.2; 351/221
[58] Field of Search .................... 250/201.2; 351/221; 356/373, 375

[56] References Cited

U.S. PATENT DOCUMENTS

| | | | |
|---|---|---|---|
| 4,686,360 | 8/1987 | Gorgon | 250/201.2 |
| 4,881,808 | 11/1989 | Bille et al. | 351/221 |
| 4,936,676 | 6/1990 | Stauffer | 356/375 |
| 5,162,641 | 11/1992 | Fountain | 250/201.2 |

FOREIGN PATENT DOCUMENTS 47-18787 5/1972 Japan ...................................... 356/375

Primary Examiner—Constantine Hannaher
Attorney, Agent, or Firm—Thomas M. Freiburger

[57] ABSTRACT

A system and method for detecting, measuring and correcting for movements of a target in a medical analytic or surgical system utilizes generally the principles of confocal microscopy. A pinhole and photodetector combination is positioned behind optics of a system for delivering an ophthalmic surgery laser beam, for example. As in a confocal microscope, the optics are arranged such that a beam waist is formed precisely at the pinhole when the target is in its nominal position. When the target moves from its nominal position in the depth direction, the signal from the pinhole/photodetector combination decreases. The change in the signal can be used to drive the objective lens of the optics so as to move with the moving target. Alternatively, the signal can be used to drive the pinhole/photodetector assembly so as to again attain peak signal, in this way allowing the target's shift to be measured.

12 Claims, 5 Drawing Sheets

SYSTEM FOR DETECTING, CORRECTING AND MEASURING DEPTH MOVEMENT OF A TARGET

REFERENCE TO RELATED APPLICATION

This application is a continuation-in-part of application Ser. No. 655,919, filed Feb. 19, 1991, now U.S. Pat. No. 5,162,641.

BACKGROUND OF THE INVENTION

This invention relates to optics, and it is concerned more specifically with detection of, measuring of and correction for movement of an optical target during a procedure involving the optics, such as a medical or industrial procedure involving a laser beam focused on the target.

In laser delivery systems, and particularly in systems for delivering a surgical laser beam toward target tissue which is being operated upon, it is important either to have the target totally immobilized during the procedure, or to quickly follow or "track" optically the target movements occurring. These movements can, in a surgical setting, be caused by the patient's being unable or unwilling to sufficiently control voluntary musculature, and/or by operation of involuntary musculature (e.g. heartbeat, breathing). This is true for imaging systems which present to a user images or data relating to the configuration or topography of the target and/or relating to the location of a laser beam's focus, when fired, on or in the target. It also is true for the focussing system itself.

The principle of confocal microscopy is well known. The principle involves the focussing of an optical system on an object or position in front of an objective lens, with a second focal point being located at a pinhole in the system behind the objective lens. If the depth of origin of specularly reflected light entering the system through the objective lens changes, the intensity of light at an image plane behind the pinhole becomes less due to shifting of the second focal point or beam waist away from the pinhole.

Bille U.S. Pat. No. 4,881,808 disclosed an imaging system for determining the location of an object such as the cornea of the human eye. Bille's disclosed system utilized the principles of confocal microscopy in determining the location of a series of points on the cornea, in order to draw a picture electronically of the corneal shape and thus to define its position In determining the location of each point, Bille moved the pinhole in a confocal microscope system in order to find the pinhole location wherein light was focussed through the pinhole, i.e. the maximum light intensity on a photodetector behind the pinhole. Each point taken in Bille's system gave a relative depth for a particular aiming location of the imaging system. With a number of such points taken, each at a different aiming location, Bille's system was able to obtain coordinates of a series of points thereby drawing a picture of the location of the curved shape being imaged. The system of the Bille patent therefore operated in a manner similar to conventional confocal microscopy, in that transverse shifting of point locations investigated resulted in a collection of measurements which could be used to generate topographical mapping of the object being imaged.

Bille's system differed from the present invention principally in that Bille's purpose and objective were to image a shape such as an ocular cornea, and to determine the location of that shape. The system of the present invention is not an imaging system but rather a system for detecting movements of a target (such as an ocular cornea) during a procedure such as laser ophthalmic surgery. The system of the invention has the objective of monitoring the depth of a point of specular reflection along a single optical axis line, not imaging the shape of the cornea or locating a series of points in space.

Further, a principal purpose of the invention is to correct for and follow depth movements of a target such as the cornea of an eye during a surgical procedure; this can be accomplished by driving an objective lens (or other optics) of the system in response to the changes in intensity of light imaged on a photodetector behind a pinhole caused by changes in the depth position of the specular reflection point on the target.

SUMMARY OF THE INVENTION

In accordance with the present invention, a system for detecting, measuring and/or correcting for movements of a target in a laser targeting procedure uses the principles of confocal microscopy, in a preferred embodiment, in order to track the changes in depth position of the target.

A pinhole and photodetector combination is positioned behind optics of a system for delivering a laser beam, for example an ophthalmic surgical laser beam. The optics of the system of the invention are so configured that a beam waist is formed precisely at the pinhole when the target of the laser beam is in its nominal position. Thus, maximum light intensity is directed onto the photodetector behind the pinhole.

When the target moves from its nominal position, changing its depth distance from the optical system, the signal from the pinhole/photodetector combination decreases. The change in this signal can be used to drive the objective lens of the optical system in or out so as to move with the moving target. When the target moves, a signal decrease is experienced in either direction of target movement, i.e. toward or away from the objective lens. When this occurs the objective is moved in such a way as to again move the focus onto the target's reflective surface, maximizing the signal at the photodetector. Monitoring of the focus condition may be accomplished by dithering the pinhole/photodetector assembly to determine which direction of movement will produce an increase in signal. As long as the signal is in balance at each end of the dither, no correction is needed, at which point the signal will be maximal. When the appropriate direction is identified by an out of balance condition, the objective is moved in that direction until the signal at the photodetector is again balanced/maximal, thus signifying that the beam waist is again located at the pinhole (this may involve movement past maximum, then return to maximum). The objective is thereby again in a position to focus the laser beam at the correct depth at the target. This depth may not be the same depth as the surface from which the reflected light is received, but in a fixed relationship with that depth.

In another implementation or embodiment of the system, the photodetector signal can be used to drive movements of the pinhole/photodetector assembly so as to move to a new position wherein peak signal is again attained. The change in position of the pinhole can be used to determine the degree of depth change at the target, giving a quantitative measurement.

It is therefore among the objects of the present invention to provide a relatively simple and accurate depth movement detection, correction and/or measurement system for use in conjunction with a laser operating procedure, particularly where the operating laser is folded onto the same beam path so as to use a common objective lens. These and other objects, advantages and features of the invention will be apparent from the following description of preferred embodiments, considered along with the accompanying drawings.

DESCRIPTION OF THE DRAWINGS

FIG. 4 demonstrates the reflection of illuminating light from the non-focal position.

DESCRIPTION OF PREFERRED EMBODIMENTS

Figure 1:
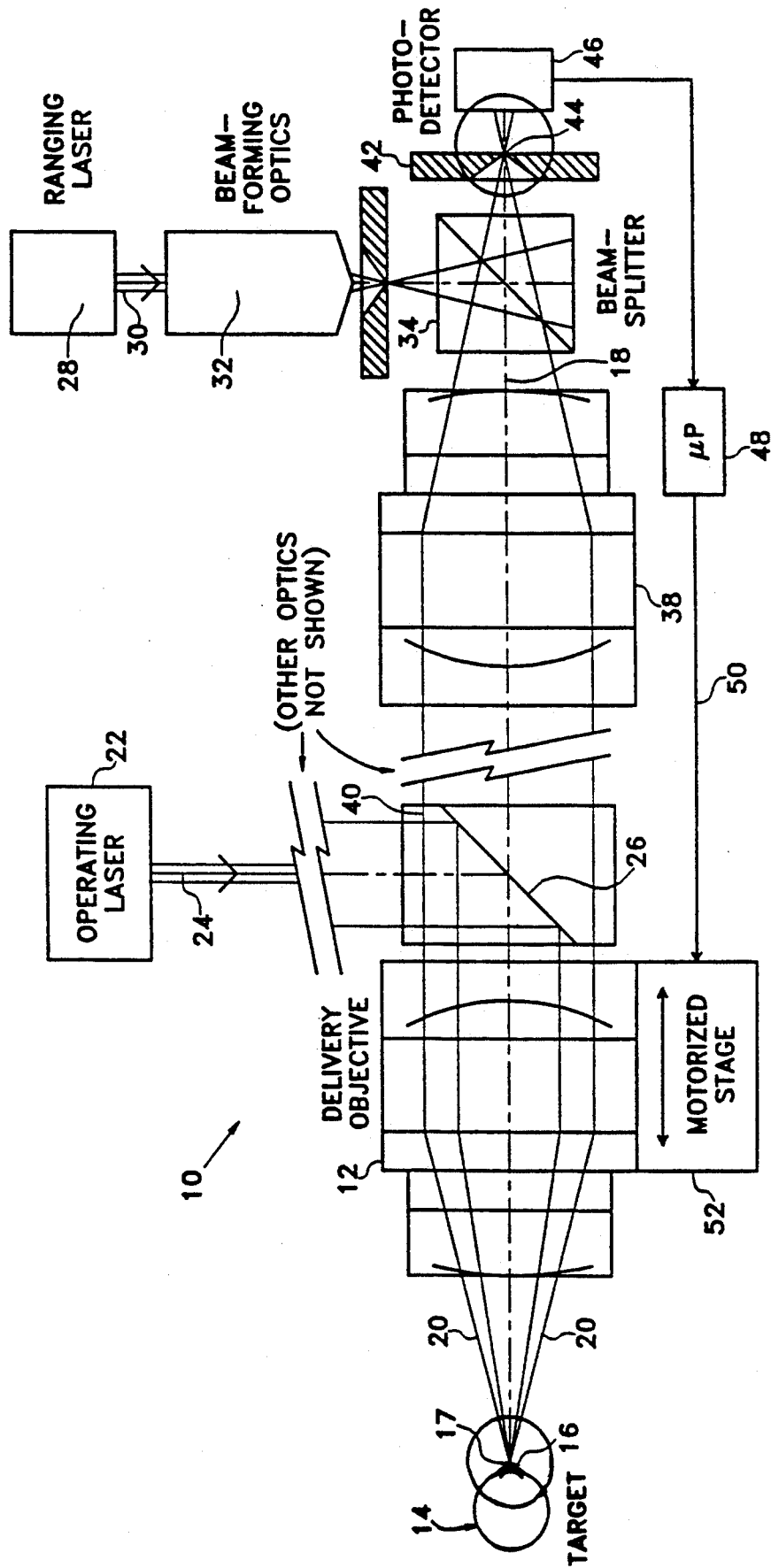
FIG. 1 is a schematic diagram showing an optical system exhibiting the principles of the present invention, for determining range of a target and/or for following movements of the target.

In the drawings, FIG. 1 shows an optical system 10 illustrating the principles of the present invention. In the system 10, a delivery objective lens or objective lens assembly 12 is positioned adjacent to a target 14, illustrated as the cornea 16 of a human eye. A front reflective surface 17, in this case a tear layer on the cornea, is positioned nominally on the optical axis 18 of the optical system 10 and of the objective lens assembly 12, and, at least nominally, at the focus or focal point of the objective lens system 12. This is indicated by edge rays 20 in FIG. 1. The actual target for laser operation often will not coincide with the reflective surface 17, particularly in ophthalmic surgery. It may be inside the cornea or deeper in the eye, even the retina, and it may be off-axis. The reflective surface 17 is a reference point, with the operative target having a fixed relationship to that surface.

FIG. 1 also shows an operating laser 22, the beam 24 of which is folded onto the optical axis 18 of the system using a beam splitter 26. Thus, the operating laser 24 is focussed by the objective lens assembly 12 onto the target, which again may not coincide with the reflective surface 17.

A second laser 28 is also shown in FIG. 1. The laser 28 emits a low power laser beam, for illumination purposes only. Its laser beam 30 passes through beam-forming optics 32 and is folded onto the optical axis 18 of the system 10 using a beam splitter 34. As indicated, the illumination beam passes through other optics which are not shown in FIG. 1, approaching the delivery objective lens assembly 12 as a parallel or nearly parallel beam. The illumination beam is then focussed as indicated by the edge rays 20 onto the target, substantially at the focal point of the objective.

At the same time, as noted above, the operative laser beam 24 is focussed using the same objective 12 so that it operates in a narrow depth of field at the site which is being operated upon. Different delivery optics back of the objective cause the focus of the operating beam to occur at a different point from that of the illuminating beam, although both pass through the same objective 12. FIG. 1 is schematic and is not accurate in scale and as to angles.

FIG. 1 also shows a collimation/decollimation lens assembly 38 which forms a part of the optics of the system 10. The combination of beam forming optics 32 and lens assembly 38 expand the illumination beam 30, and the lens assembly 38 focusses return reflected light traveling in the opposite direction. Thus, when the target (e.g. the eye 14) is precisely at the correct distance from the delivery objective 12, a reflection of the illumination light travels back into the system, having been specularly reflected from the tear layer 17 on the surface of the cornea. The edge beam rays 20 schematically illustrate that the reflected light returns through the objective 12 and again travels in a parallel path (or substantially parallel, similar to the path of the illumination light) indicated at 40. The edge rays are then indicated as being focussed by the collimation/ decollimation lens assembly 38, through the beam splitter 34 and through a pinhole structure 42. A pinhole of the pinhole structure is located precisely at a beam waist 44, so that substantially the entire reflected light beam passes through the pinhole via the location of the beam waist 44.

Back of the pinhole structure 42 is a photodetector 46, which receives all of the reflected light passing through the optics when the beam waist is positioned properly at the pinhole, as illustrated in FIG. 1. Thus, maximum intensity is detected at the photodetector 46 in this condition.

A microprocessor 48 receives the light intensity signal from the photodetector 46, and in response sends a signal, indicated on line 50, to a motor or other servo device 52. The motor or servo device, as illustrated, is connected to the delivery objective lens assembly 12 and is capable of moving the objective in and out depthwise in response to signals from the microprocessor 48. As described earlier, if the signal at the photodetector becomes weaker, the system must search for a new position of the target insofar as depth is concerned. Thus, when the signal weakens as determined at the microprocessor 48, the microprocessor can direct the motor 52 to move the objective in a given direction exploring for a stronger or weaker signal, then move in the appropriate direction. Alternatively, if the pinhole/photodetector assembly is being dithered in and out very quickly, as described above, it can determine by means of the imbalance in the signal which direction produces an increase in signal. When the correct direction is ascertained, the objective assembly 12 is moved in that direction until the signal again reaches maximum.

The signal at the photodetector becomes weaker on shifting of the target because the beam waist 44 becomes displaced from the pinhole 42. This effect is schematically indicated in FIGS. 2, 3, 4, 5 and 6.

Figure 2:
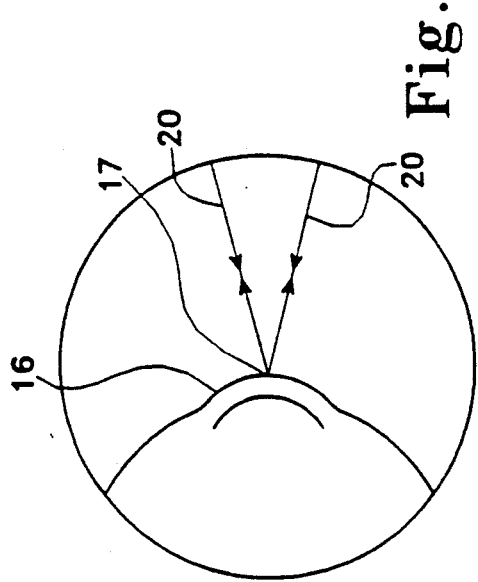
FIG. 2 is a schematic view showing in detail the reflection of light from a target (the tear layer on the cornea of an eye) with the target positioned generally at the focal point of a delivery objective lens.

In FIG. 2, the cornea tear layer 17 is shown at the precise focus of the objective. Light is reflected back along the same path, as indicated by the edge rays 20. At the other end of the system, as shown in FIG. 3, the beam waist 44 occurs precisely at the pinhole, causing the full intensity of the reflected light to be projected onto the sensing surface 54 of the photodetector 46.

Figure 4:
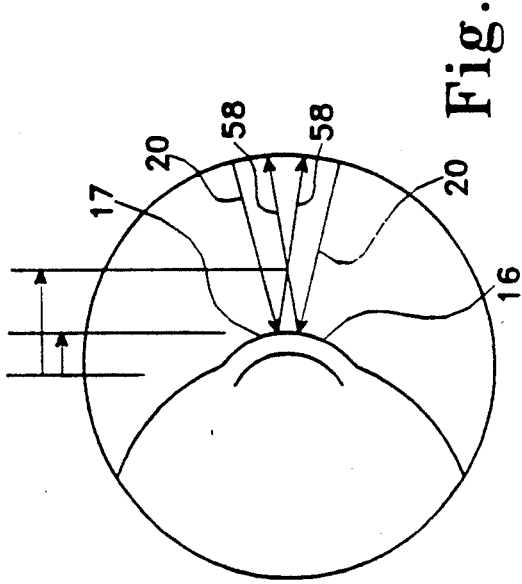
FIG. 4 is a detail schematic view similar to FIG. 2 and juxtaposed with FIG. 2, showing the movement of the target object (the eye) to a new depth position in which the reflective surface is not at the focal point of the delivery objective lens.

If, on the other hand, the target and consequently, the reflective surface 17, are displaced in depth from the position in FIG. 2, as shown in FIG. 4, the optics of the returning reflected light are different. FIG. 4 shows that the cornea has moved closer to the system 10, i.e. to the delivery objective 12. Edge ray 20 of the approaching illumination beam strike the reflecting surface 17 of the tear layer not in focus, producing reflected return rays 58 which do not follow the edge ray paths shown in FIG. 1. The effect is shown in FIG. 6.

Figure 5:
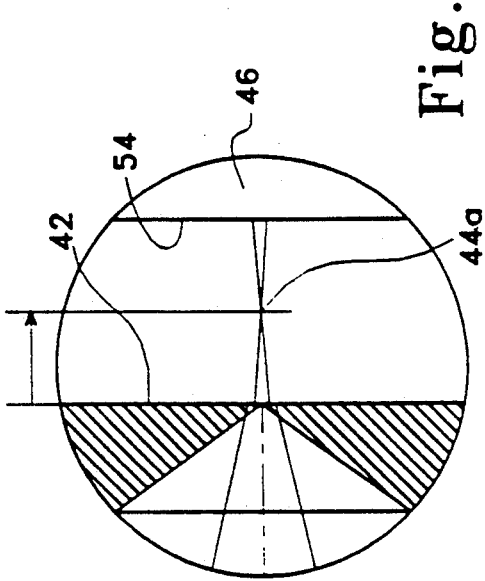
FIG. 5 is a detail schematic view similar to FIG. 3, showing the cropping of light at the pinhole, due to displacement of the target as demonstrated by FIGS. 4 and 2.
Figure 6:
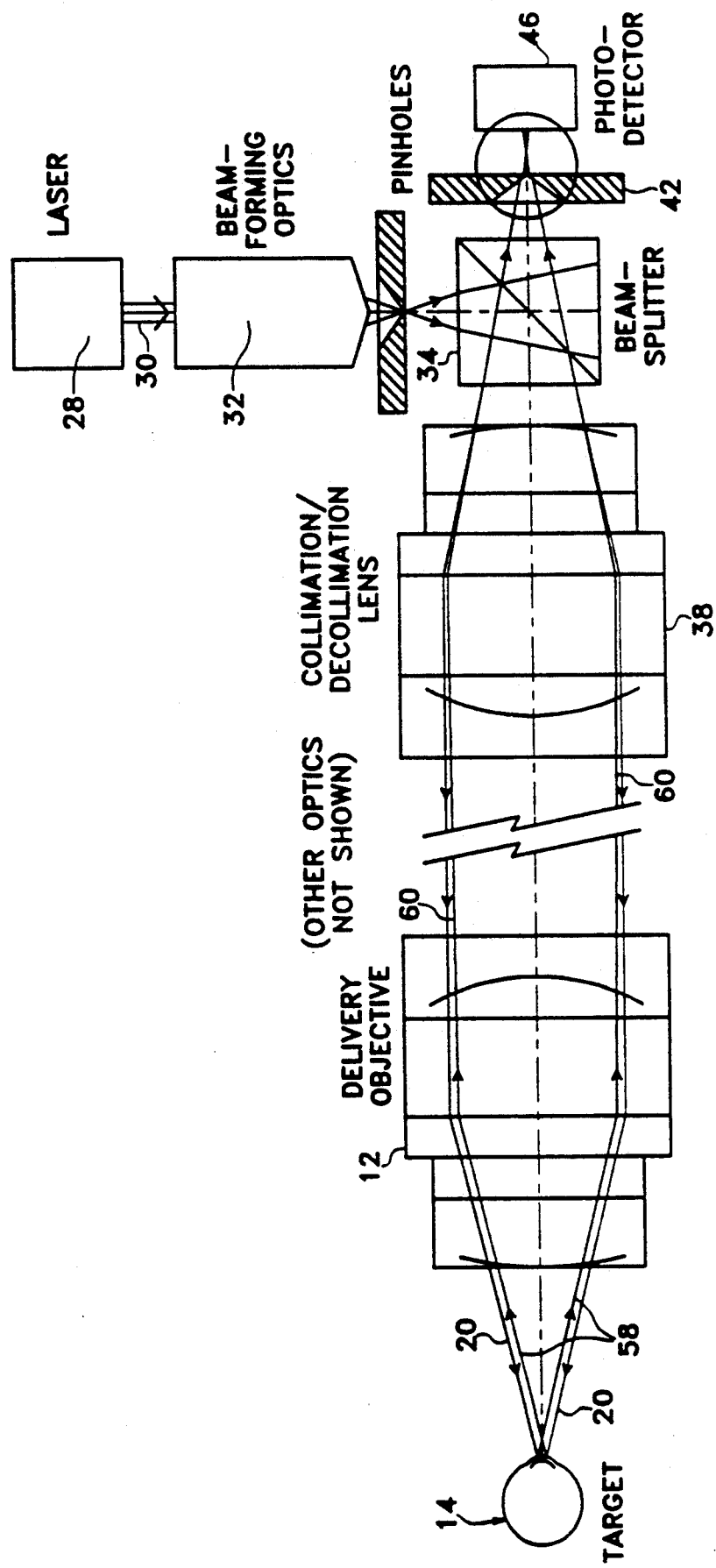
FIG. 6 is a schematic system diagram similar to FIG. 1, but showing the different paths of reflected light through the system when the target is displaced as in FIG. 4, resulting in the beam waist displacement indicated in FIG. 5.

FIG. 6 shows that the reflection of the illuminating beam, indicated as lines 58, passes through the delivery objective closer to the center of the objective. These return rays are of generally the same angulation (depending on the target curvature) as the illuminating edge rays 20, although inverted. Thus, since they pass through the objective closer to its center, they are divergent at 60, where the illuminating beam was substantially parallel. This causes the rear focal point or beam waist 44 to be pushed back, to a point indicated at 44a in the detail schematic view of FIG. 5. This is the point where the return rays would intersect, but the pinhole structure 42 crops all but a very small central region of the returning beam. Thus, the reflected light which actually reaches the photodetector plane 54 is of much less intensity than was the case with the target properly positioned (see FIGS. 1 and 3).

Figure 3:
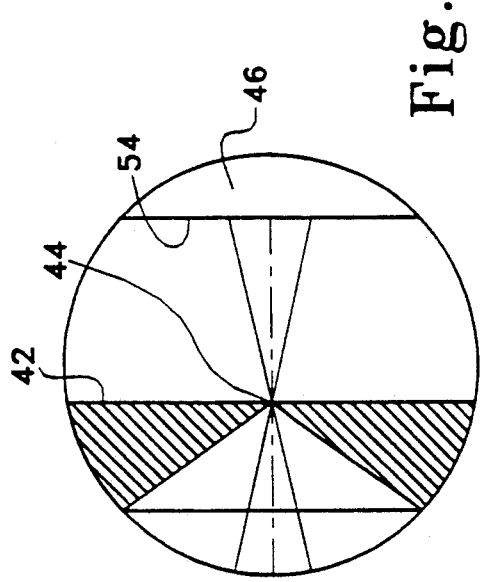
FIG. 3 is a schematic detail view showing the light reflected from the target surface in FIG. 2 being focussed at a rear focus or beam waist which is precisely located at a pinhole in the system.

FIGS. 2 and 4 illustrate that the change in position of the reflective surface 17 causes a greater change in position of the focus of the edge rays of the illumination beam, leading to the beam waist shift shown in FIGS. 3 and 5.

Figure 7:
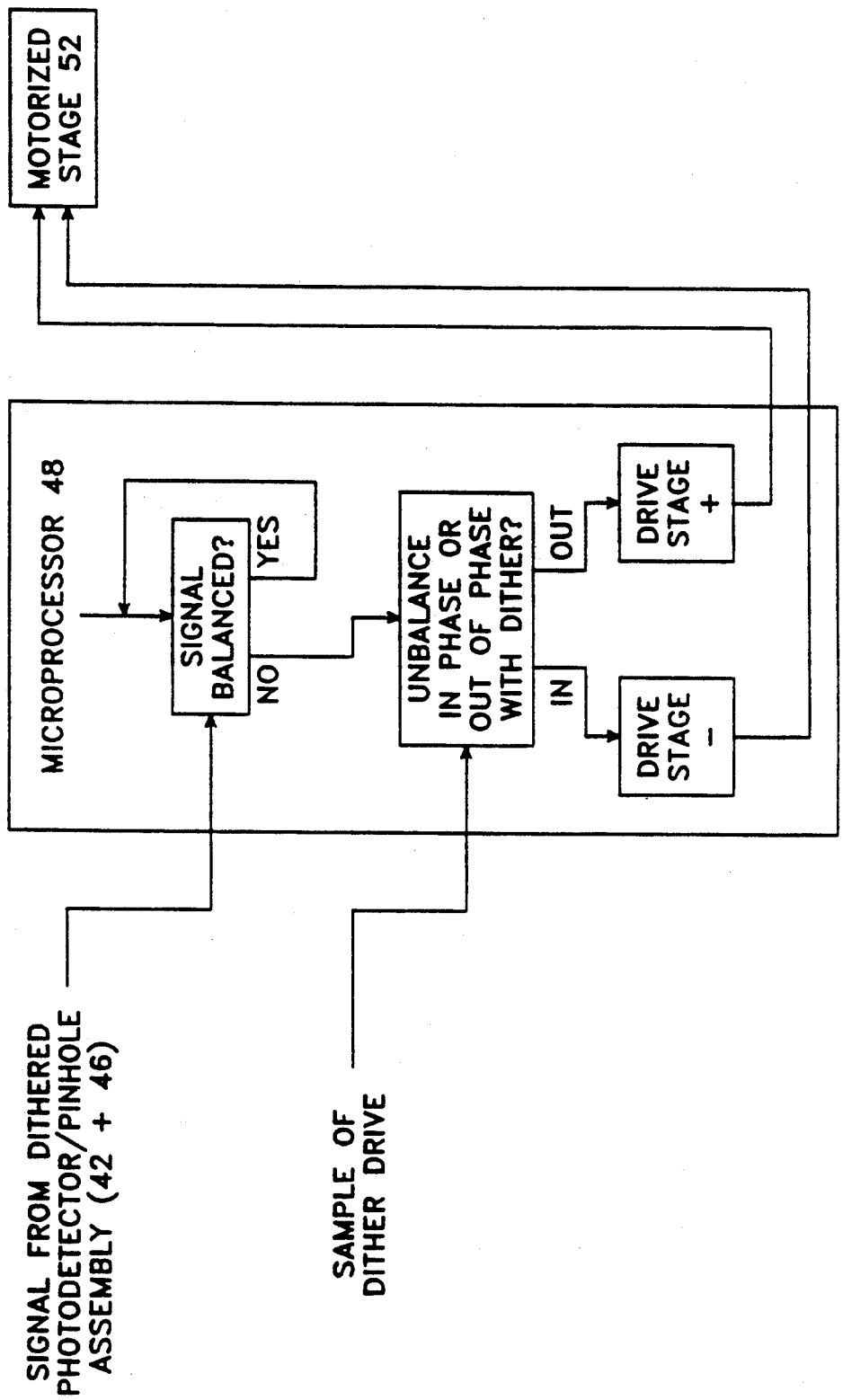
FIG. 7 is a simple flow chart showing operation of a target following system forming a part of the invention.

FIG. 7 is a simplified flow chart showing the control of the motor or servo device 52 by the microprocessor 48, in response to changes of signal at the photodetector 46.

Figure 8:
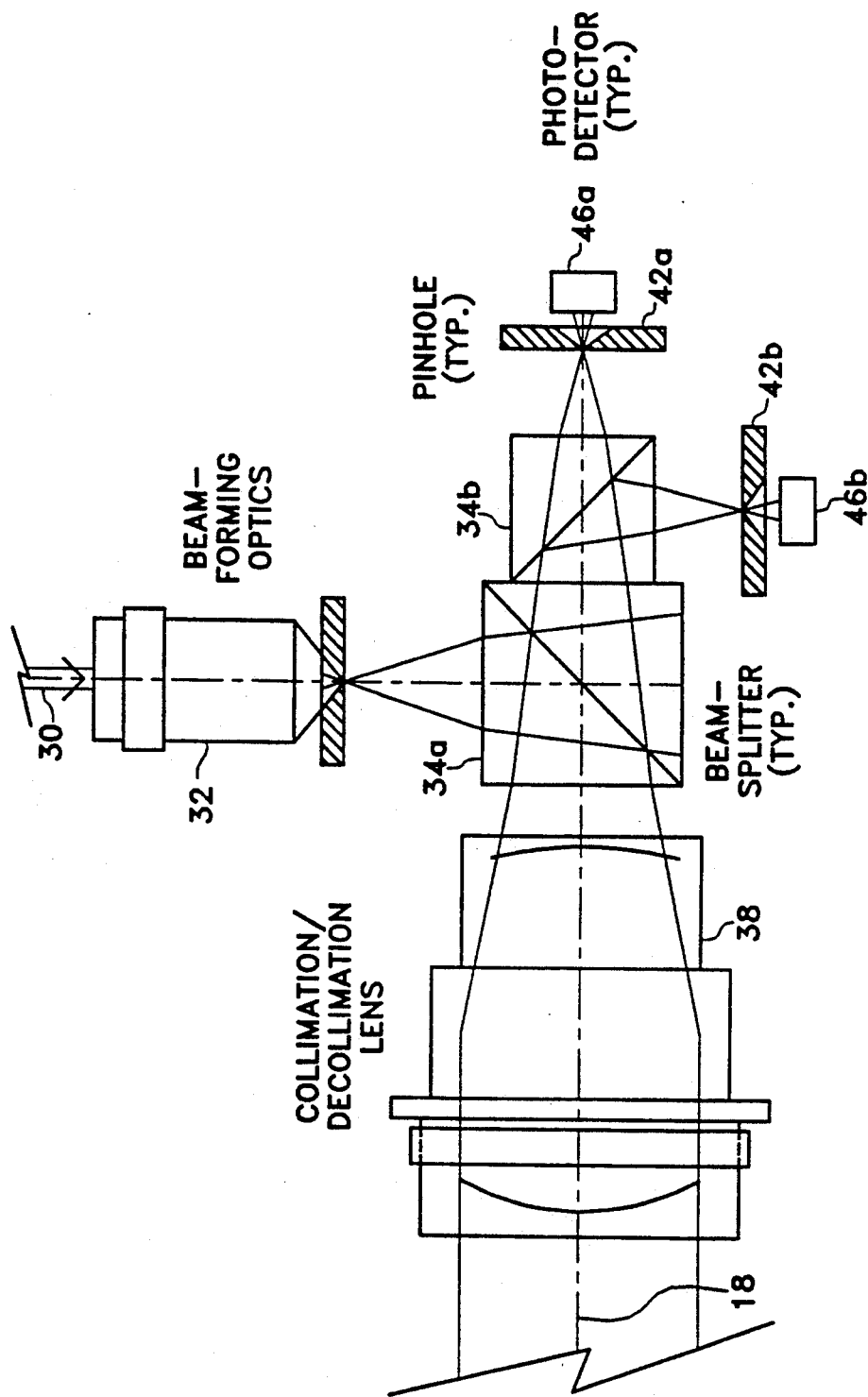
FIG. 8 is a schematic diagram showing another embodiment of the invention.

FIG. 8 shows the relevant portions of FIG. 1, revised to permit the use of the electronic equivalent of mechanical dithering of the pinhole/photodetector assembly. The single beam splitter 34, pinhole structure 42, and photodetector 46 of FIG. 1 are replaced by the double beam splitters 34a and 34b, pinhole structures 42a and 42b, and photodetectors 46a and 46b of FIG. 8. In this implementation, the pinholes are set to axially differing locations with respect to the respective beam waists—for example, one as in FIG. 3 and the other as in FIG. 5—and microprocessor 48 alternately or simultaneously samples and compares the signals from the two photodetectors, rather than monitoring the varying signal from one dithered pinhole/photodetector assembly. If one pinhole is axially located (when the system is nominal) at its respective waist and the other is not, the strategy for tracking motions of the target is as above: move the objective lens so as to maximize the signal from that photodetector, which should be maximized when the system is nominal. The direction of motion is determined by whether the ratio of the two signals is greater or less than the ratio in the nominal condition. In other words, if the second pinhole 42b is nominally back of the beam waist (closer to the detector 46b) as an example, and the signal at photodetector 46a becomes weaker due to target movement, the correct direction for adjustment of the objective lens becomes apparent by looking at whether the detector 46b signal becomes weaker or stronger. A stronger signal in this example indicates the target has moved closer, pushing the beam waist closer to the pinhole 42b.

An enhanced range for acquiring the target is obtained by locating one pinhole axially ahead of its respective waist and the other axially behind its respective waist in such a manner that the two signals are equal (but neither maximized) when the system in nominal; in this case the strategy for tracking motions of the target is to move the objective lens so as to reattain the balanced condition (the direction of motion is determined by which photodetector has the greater signal).

In the latter case it is advantageous to mathematically normalize the electronic signal from each of the photodetectors to the intensity of the reflected light by dividing such signal electronically by the sum of the electronic signals from both photodetectors. A known relationship between the two photodetectors (which, as described above, may be equality) is then established between such resulting normalized detected light levels. In this way the method is rendered insensitive to changes in the light level of illuminating light beam or in the reflectance of the reflective surface associated with the target.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A method for detecting and correcting for movements in a depth direction of a target at which a treatment laser beam is directed, comprising, directing an illuminating light beam from an illuminating light source toward the target through an objective lens means, to a focus at the position of a reflective surface associated with the target, providing a pinhole structure with a pinhole, in an optical system behind the objective lens means, reflecting the illuminating light beam off the reflective surface associated with the target, and receiving the reflected light through the objective lens means and through the optical system to a rear focus or beam waist of the reflected light at the pinhole when the target is in a nominal position with the reflective surface at the focus of the illuminating light beam, directing a treatment laser beam through the objective lens means to a treatment laser focus at the target, which may be a different focus from the focus of the illuminating light beam but in a known relationship thereto, detecting the level of light passed through the pinhole with a photodetector means positioned behind the pinhole, determining, in response to a reduction in light intensity sensed by the photodetector, which direction of travel of the objective lens means will result in a gain in light intensity, and moving the objective lens means outwardly toward the target or inwardly away from the target in response to a reduction in light intensity sensed by the photodetector means behind the pinhole and in the appropriate direction as determined by the determining step, until the light level sensed at the photodetector means is maximized thereby indicating the location of the beam waist at the pinhole and the location of the reflective surface at the focus of the illuminating light beam, and thereby refocussing the treatment laser beam at the proper depth at the target.

2. The method of claim 1, wherein the reflective surface associated with the target is a tear layer of the cornea of a human eye, and wherein the treatment laser beam is of such power and repetition rate as to be capable of therapeutic treatment inside the eye.

3. The method of claim 1, wherein the movement of the objective lens means to maximize sensed light level is accomplished by monitoring an intensity signal from the photodetector means in a microprocessor, and automatically directing a motor means with the microprocessor to move the objective lens mean in a way as to maximize sensed light intensity after a decrease in light level is detected.

4. The method of claim 1, wherein the determining step and the movement of the objective lens means to maximize sensed light level is accomplished by providing a second pinhole structure with a second pinhole and a second photodetector means positioned behind the second pinhole, splitting off a portion of the reflected light en route to the rear focus or beam waist with a beam splitter to form a second beam waist generally at the second pinhole, establishing a known relationship between the two beam waists/pinholes in which one of the beam waists is axially offset from the pinhole when the other beam waist is precisely at the pinhole, and, when it is determined from a change in light intensity at one of the photodetector means that a change in the depth of the target has occurred, determining from the change in signal at the other photodetector means whether the direction of target movement was closer or farther away, then moving the objective lens in the appropriate direction to again maximize the light signal at the one photodetector means.

5. A method for detecting and correcting for movements in a depth direction of a target at which a treatment laser beam is directed, comprising, directing an illuminating light beam from an illuminating light source toward the target through an objective lens means, to a focus at the position of a reflective surface associated with the target, providing at least one pinhole structure with a pinhole, in an optical system behind the objective lens means, reflecting the illuminating light beam off the reflective surface associated with the target, and receiving the reflected light through the objective lens means and through the optical system to a rear focus or beam waist of the reflected light at a nominal position relative to the pinhole when the target is in a nominal position with the reflective surface at the focus of the illuminating light beam, directing a treatment laser beam through the objective lens means to a treatment laser focus at the target, which may be a different focus from the focus of the illuminating light beam but in a known relationship thereto, detecting the level of light passed through the pinhole with a photodetector means positioned behind the pinhole, and means outwardly toward the moving the objective lens target or inwardly away from the target in response to a change in light intensity sensed by the photodetector means behind the pinhole, until the light level sensed at the photodetector means is essentially that level determined at the nominal position, thereby indicating the location of the beam waist at the nominal position relative to the pinhole and the location of the reflective surface at the focus of the illuminating light beam, and thereby refocussing the treatment laser beam at the proper depth at the target.

6. The method of claim 5, wherein two said pinhole structures are provided, each with a pinhole and with a photodetector means behind the pinhole, and including splitting off a portion of the reflected light en route to the rear focus or beam waist with a beam splitter to form two beam waists generally at the respective pinholes but each displaced axially therefrom, one forward of and one back of the pinhole, in a nominal position with the reflective surface at the focus of the illuminating light beam, establishing a known relationship between the detected light levels at the two photodetector means for the nominal position, and, when it is determined from changes in light intensity at the photodetector means that a change in the depth of the target has occurred, determining from the directions of changes in signal at the two photodetector means whether the direction of target movement was closer or farther away, then moving the objective lens in the appropriate direction to again establish said known relationship between the detected light levels at the two photodetector means, representing said nominal position.

7. The method of claim 6, wherein the known relationship between the detected light levels at the two photodetector means for the nominal position is equality, i.e. with the light levels in balance.

8. The method of claim 6, wherein the electronic signal from each of the photodetectors is mathematically normalized to the intensity of the reflected light by dividing such signal electronically by the sum of the electronic signals from both photodetectors, and the known relationship is established between such resulting normalized detected light levels, thereby rendering the method insensitive to changes in the light level of the illuminating light beam or in the reflectance of the reflective surface associated with the target.

9. The method of claim 8, wherein the known relationship between the normalized detected light levels for the nominal position is equality.

10. An optical system for detecting and correcting for movements in a depth direction of a target at which a treatment laser beam is directed, the treatment laser beam passing through a common objective lens with the optical system, comprising, objective lens means at the front of the optical system, to be positioned adjacent to a target lying on an optical axis of the objective lens means and generally at the focus of the objective lens means, illumination means for sending an illuminating light beam toward the target through the objective lens means, to an illuminating beam focus at the position of a reflective surface associated with the target when the target is in a nominal position, optical means behind the objective lens means for receiving light reflected from the reflective surface associated with the target and passed through the objective lens means and for focussing the reflected light to a rear focus or beam waist, a pinhole structure with a pinhole located in a nominal position relative to the beam waist when the target is in a nominal position with the reflective surface at the illuminating beam focus, photodetector means behind the pinhole structure and positioned to receive the illuminating beam as reflected from the reflective surface of the target and passed through the objective lens means, the optical means and the pinhole, the photodetector means including means for measuring the intensity of light received through the pinhole, treatment laser means for producing a treatment laser beam, with means for folding the treatment laser beam into the optical system so as to pass the treatment laser beam through the objective lens means toward a treatment laser focus at the target, and target following means connected to the photodetector means and including driving means for moving the objective lens means outwardly toward the target or inwardly away from the target, the target following means including means responsive to a change in light intensity at the photodetector means, for determining which direction of movement of the objective lens means will follow the movement of the target and for moving the objective lens means until the light level sensed at the photodetector means again indicates that the location of the beam waist is at the nominal position relative to the pinhole and thus that the location of the reflective surface is at the focus of the illuminating light beam, whereby the focus of the treatment laser beam is properly relocated relative to the target as desired.

11. A system according to claim 10, wherein the reflective surface associated with the target is a tear layer of the cornea of a human eye.

12. A system according to claim 10, wherein the means for determining direction of movement includes a second pinhole structure with a second pinhole and a second photodetector means positioned behind the second pinhole, means for splitting off a portion of the reflected light en route to the rear focus or beam waist with a beam splitter to form a second beam waist generally at the second pinhole, means establishing a known relationship between the two beam waists/pinholes in which one of the beam waists is axially offset from the pinhole when the other beam waist is precisely at the pinhole, and means responsive to a change in light intensity at one of the photodetector means indicating that a change in the depth of the target has occurred, for determining from the change in signal at the other photodetector means whether the direction of target movement was closer or farther away, whereby the objective lens can then be moved in the appropriate direction to again establish the nominal position of the beam waist relative to the pinhole.

* * * * *

UNITED STATES PATENT AND TRADEMARK OFFICE
CERTIFICATE OF CORRECTION

PATENT NO. : 5,286,964
DATED : February 15, 1994
INVENTOR(S) : William D. Fountain It is certified that error appears in the above-indentified patent and that said Letters Patent is hereby corrected as shown below:

On the Title Page, under Item [19], after "Fountain" insert --et al.-- and in Item [75] please add as a second inventor: --Jan Wysopal, Livermore, California--.

Column 7, line 27, correct "mean" to read --means--.

Column 8, line 9, delete the entire line.

Column 8, line 10, following "lens" insert --means outwardly toward the--.

Signed and Sealed this

Twelfth Day of July, 1994

Attest:

BRUCE LEHMAN

Attesting Officer   Commissioner of Patents and Trademarks